United States Patent

Hartman et al.

[11] 4,108,182
[45] Aug. 22, 1978

[54] RECIPROCATION VITREOUS SUCTION CUTTER HEAD

[75] Inventors: Robert M. Hartman, Clearwater; Arthur F. Trott, Largo, both of Fla.

[73] Assignee: Concept Inc., Clearwater, Fla.

[21] Appl. No.: 769,191

[22] Filed: Feb. 16, 1977

[51] Int. Cl.$^2$ .............................................. A61B 17/32
[52] U.S. Cl. ....................................... 128/305; 30/133
[58] Field of Search ............... 128/305, 303, 310, 276; 30/133, 217, 220, 272 A

[56] References Cited

U.S. PATENT DOCUMENTS

| | | | |
|---|---|---|---|
| 3,618,611 | 11/1971 | Urban | 30/133 X |
| 3,776,238 | 12/1973 | Peyman et al. | 128/305 |
| 3,902,498 | 9/1975 | Niederer | 128/305 |
| 3,945,375 | 3/1976 | Banko | 128/305 X |

*Primary Examiner*—John D. Yasko
*Attorney, Agent, or Firm*—Gipple & Hale

[57] ABSTRACT

A surgical instrument comprising a housing with a motor and source of power contained in the housing. A removable sheath is placed over the housing and a cutter assembly is removably mounted to the housing so that the housing is protected from external materials and contamination. The cutter assembly has a body, a tube projecting from the body, a reciprocating blade positioned in the tube and a cam drive transfer mechanism mounted in the cutter body which transmits motion to the blade from the motor shaft. The tube defines an aperture in its side and the blade as it reciprocates in combination with the walls defining the aperture shears vitreous material entering the hole. A second passage is formed in the cutter body communicating with the tube to allow pressure differentials to be exerted to the tube.

The cutter head and removable protective sheath are replaced after each successive operation in order to eliminate patient-to-patient cross contamination.

12 Claims, 17 Drawing Figures

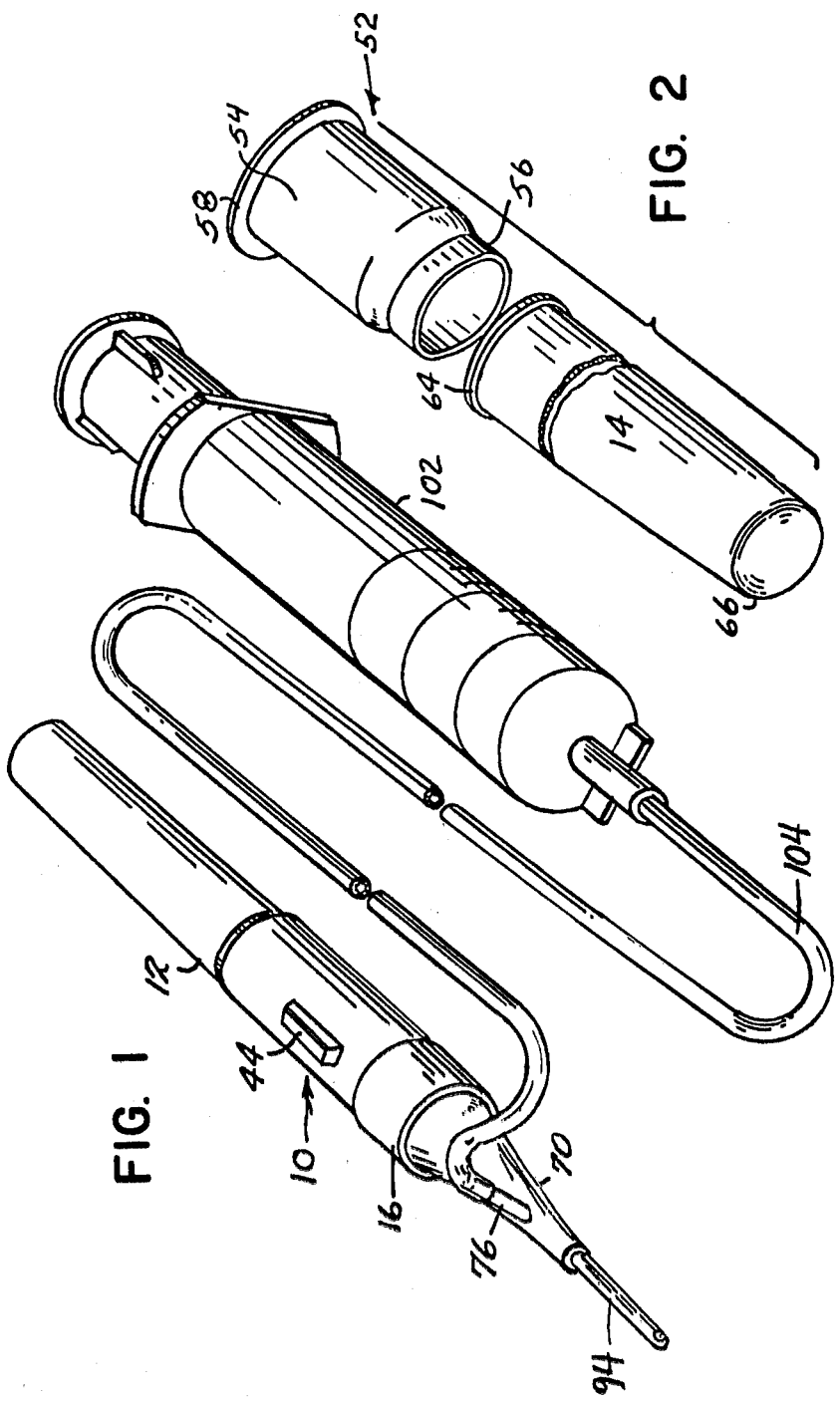

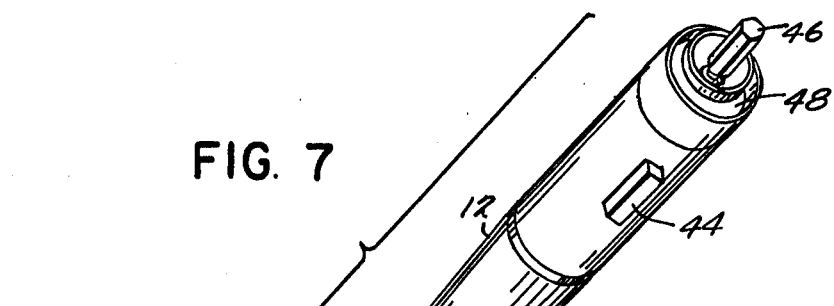
FIG. 7
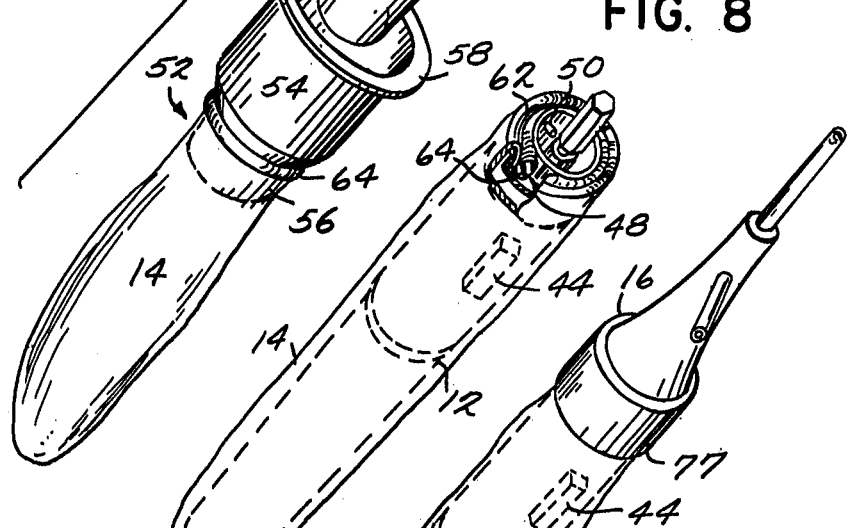
FIG. 8
FIG. 9

RECIPROCATION VITREOUS SUCTION CUTTER HEAD

BACKGROUND OF THE INVENTION

The present invention relates to a powered surgical cutter and more particularly to a sterile disposable powered surgical cutter particularly adapted to perform eye surgery by cutting and removing vitreous from inside the anterior aqueous chamber of the eye.

The role of vitreous in retinal detachment has been recognized for many years, but the vitreous remained more or less untouched until Shafter (1958) replaced it with human vitreous implant. (D. M. Shafer, The Treatment of Retinal Detachment by Vitreous Implant Transactions American Academy Ophthalmology and Otolarying. 61:194–200, 1958). Later, Michaelson described in 1960 an instrument capable of cutting the vitreous bands. (Michaelson, Transcleral Division of Mid-Vitreous Membrane Under Visual Control, British Journal of Ophthalmology, 44:634–635, 1960). Cibis in 1964 replaced the vitreous with silicon and devised instruments for cutting the vitreous bands. (P. A. Cibis, Vitreous Transfer and Silicon Injection Transactions American Academy Ophthalomology and Otolarying. 68:983–997, 1964). Freeman, Schepens, and Anastopolous introduced their vitreous scissors in 1967 (Vitreous Surgery II Instrumentation and Technique Arch. Ophthal. 77:681–682, 1967). Kasner reported on Vitrectomy in 1968 (D. Kasner Vitrectomy: A New Approach to the Management of Vitreous Highlights Ophthalmology. 11:304–309, 1968 (published in July 1969)). In addition, Machamer, Buettner and Norton in 1970 developed a vitreous cutter-sucker infusion instrument (Vitrectomy—American Academy Ophthalmology and Otolarying. Las Vegas, 1970).

A history of the development of such cutting devices is described in the AORN Journal, November 1973, Vol 18, No. 5 page 908 in an article entitled Pars Plana Vitrectomy, a New Treatment for Vitreous Disease.

DESCRIPTION OF THE PRIOR ART

The problems inherent in the techniques, methods and apparatus relating to vitreous removal are disclosed in the Annals of Ophthalmology, September 1974, page 947 in an article, entitled Anterior Vitrectomy in Cataract Surgery, Aphakic Keratoplasty and Patients with Vitreous Pathology Using a Simple Vitreophage, and in the American Journal of Ophthalmology, June 1974, page 824, in an article entitled Companied Ketratiplasty and Cataract Extraction. In accomplishing eye surgery in the anterior aqueous chamber it has been found that after the incision is made it is sometimes necessary to draw off vitreous or in turn add vitreous fluid. Apparatus for accomplishing these ends is discussed in both of the above-mentioned periodicals.

Since vitreous is composed of hyaloronic acid and collogen fiber the substance cannot be removed by suction alone, and therefore, the vitreous fibers must be incised.

Various vitreous cutting apparatus and concepts are well known in the prior art as disclosed by the following patent references.

U.S. Pat. No. 3,734,099 discloses a hand held powered surgical cutter utilizing a cutter tip having an outer fixed tubular cutter in which an inner tubular cutter is rotated. The cutter tip is inserted into the eye and the inner cutter is rotated cutting the vitreous. The pieces of the severed vitreous are then removed through the interior of the inner tubular cutter to a disposal means. U.S. Pat. No. 3,618,861 discloses another similar hand held tubular cutting apparatus adapted to cut the vitreous in the eye and suck the cut vitreous to disposal means.

The use of ultrasonic energy in a surgical instrument to cut the vitreous is taught by U.S. Pat. No. 3,806,787. The apparatus has a probe head with bores cut therein to receive both suction means adapted to remove material emulsified by the probe and fluid transfer means to transmit irrigation fluid into the eye.

Another hand held vitreous cutter is disclosed in U.S. Pat. No. 3,732,858 which utilizes a rotating blade mounted in a tube to cut the vitreous material. As the vitreous is cut suction means draw the vitreous material back up through the tube housing of the cutting blade to an area for disposal. The apparatus is also shown in another embodiment adapted to be used with infusion means for submitting or directing fluid into the eye. The present invention represents an improvement over this previously identified prior art.

One problem encountered with rotating blade assemblies is that the rotating blade can "spool" or "wind-up" the vitreous fiber around the blade. This may cause an excessive amount to be removed, with damage resulting to the interior of the eye.

The use of a reciprocating vitreous cutter apparatus is disclosed in U.S. Pat. No. 3,776,238. This reference discloses a first tube containing an inner reciprocating cutter tube powered by an electromagnetic coil positioned on the handle of the tube. The cutting action of the apparatus depends upon the sharp end of the inner tube repeatedly striking the base plate at the end of the outer tube in the manner of a cleaver. This striking action in time dulls the cutter blade and in some instances damages the cutter blade.

All of the previously disclosed apparatus must be sterilized after each operation. A common sterilization technique in hospitals is to sterilize the units with ethylene oxide. The construction of the prior apparatus is such that the cutter blade assembly which is hardest to sterilize, is difficult to reach in sterilizing processes, expensive to manufacture and is constructed to form a complex cutter assembly. Furthermore, the drive mechanism of the cutter blade assembly has to be sterilized after each use resulting in damage to the mechanism after repeated sterilization not to mention the time, labor and expense required for each sterilization.

The present invention is thus constructed with a simple disposable reciprocating cutter assembly which can be disposed of preferably after only one use. The novel use of a removable protective bag which is sealed by the disposable cutter assembly to the drive housing prevents the drive housing from being contaminated so that the drive housing can be reused within minutes or within a minute after its use in the previous operation. Due to the protective sheath, the housing does not contact surgeon or patient. The drive unit can be used and reused indefinitely without sterilization, since the sterile sheath eliminates potential cross-contamination. Because of the self contained power source the instrument can be used in the field or in other remote places where power is not available. Thus the invention provides a sophisticated low cost sterile medical instrument available for use under any environment or condition. Additionally the self-contained power source provides additional convenience since no power cords or air lines are required in the operating room.

SUMMARY OF THE INVENTION

The surgical cutter of the present invention is an improvement over appartaus and methods previously disclosed in the prior art and comprises a drive housing having motor means and a power source mounted in the drive housing. An elongated external removable cutter assembly is attached to one end of the housing. The external cutter assembly comprises an outer housing mounted to the drive housing, a drive transfer assembly mounted in the outer housing, a closed end tubular blade housing secured to the outer housing and a reciprocating blade mounted within the tubular blade housing. The reciprocating blade is urged forward in the tubular blade housing by a cam and cam follower assembly which causes the blade to pass by an aperture formed in the closed end of the tubular blade housing. A coiled spring assembly urges the blade rearwardly in the tubular blade housing when the blade is not driven forward by the cam assembly. The reciprocation of the blade within the tubular blade housing beyond the opening will shear off tissue drawn into the opening formed in the end of the tubular housing and when used with suction provided by a syringe or other suitable suction means the cut material will be drawn through the interior of the cutter tip assembly into a suitable depository. This blade, therefore does not strike the end of the tube but rather cuts the vitreous by using the walls of the tube housing. A protective sheath is adapted to fit over the drive housing and into a channel formed on the end of the drive housing so that it engages the cutter assembly to form a fluid seal. The outer housing of the cutter assembly preferably has an end skirt construction which fits over the motor end of the drive housing and its associated sheath to seal or contain the non-sterile motor unit.

Although the invention will be set forth in the claims the invention itself and the manner in which it may be made and used, may be better understood by referring to the following description taken in connection with the accompanying drawings forming a part hereof in which like reference numerals refer to like parts throughout the several views and in which:

BRIEF DESCRIPTION OF THE DRAWINGS

FIG. 1 is a perspective view showing the powered surgical cutter of the present invention;

FIG. 2 is a perspective view of the disposable sterile sheath assembly used with the powered surgical cutter;

FIG. 7 is a perspective view of the invention showing the instrument drive housing about to be placed in a sterile surgical receptacle;

FIG. 8 discloses the instrument of FIG. 7 inside the sterile sheath with the end of the instrument and sheath partially shown in cross section to show the relation of the instrument with the sheath;

FIG. 9 discloses the instrument with the cutter head placed on the sheath and drive housing and locked into position;

DESCRIPTION OF THE PREFERRED EMBODIMENT

Figure 3:
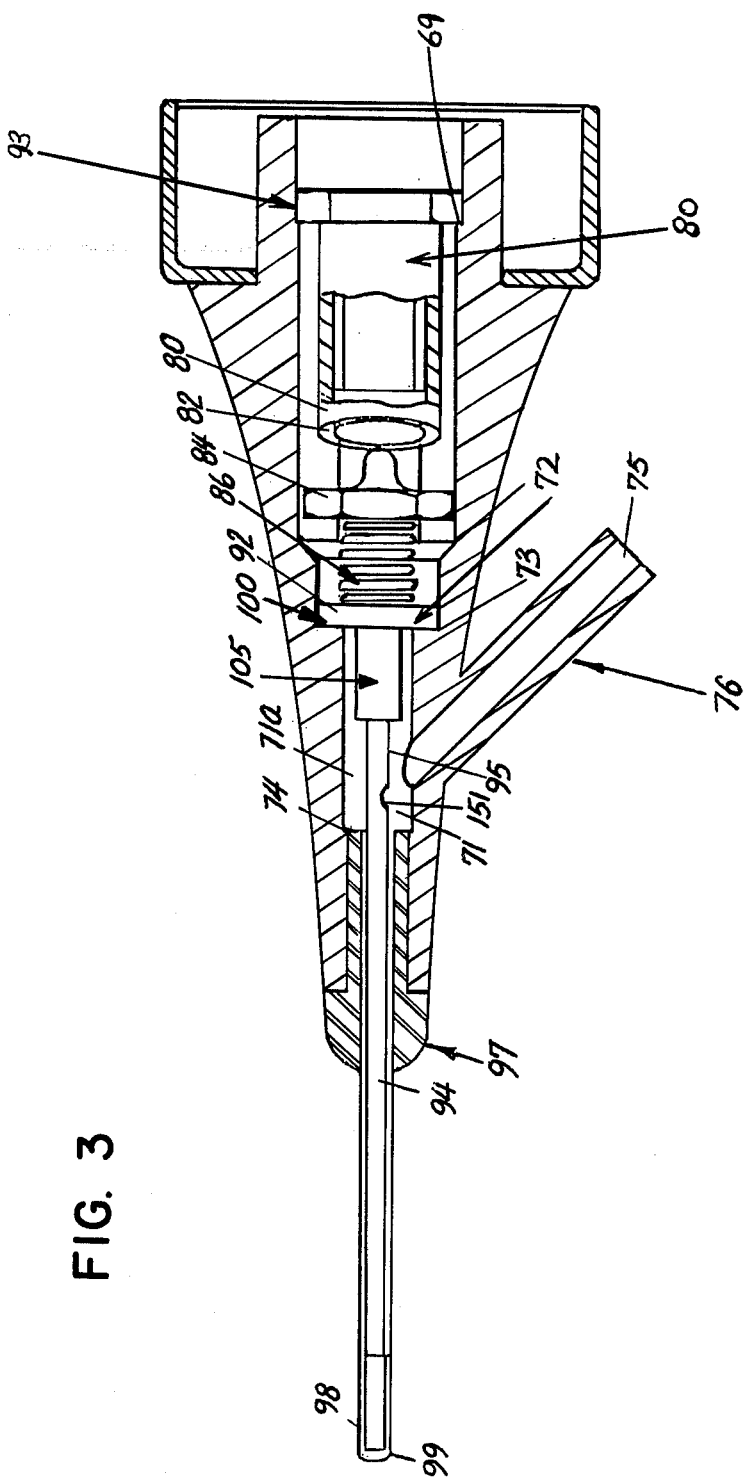
FIG. 3 is a cross-sectional view of the disposable cutter head of the invention shown in FIG. 1.
Figure 4A:
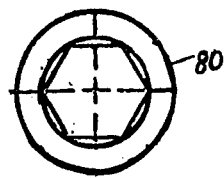
FIG. 4(a) is a rear elevational view of the cam shown in FIG. 4.
Figure 4:
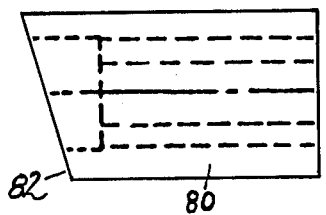
FIG. 4 is a side elevational view of the cam shown in FIG. 3.
Figure 5:
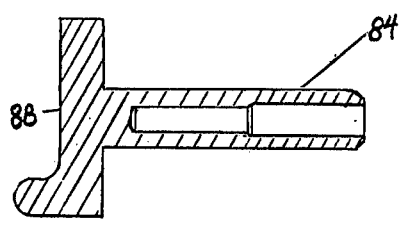
FIG. 5 is a cross sectional view of the cam follower shown in FIG. 3.
Figure 4B:
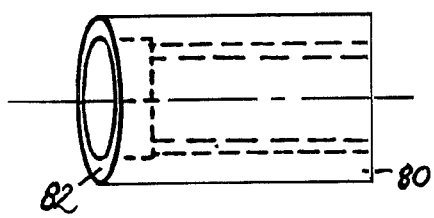
FIG. 4(b) is a side elevational view of the cam shown in FIG. 4 after a quarter rotation.
Figure 5A:
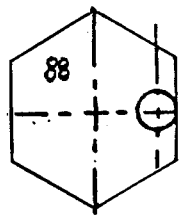
FIG. 5(a) is a front elevational view of the cam follower shown in FIG. 3.
Figure 5B:
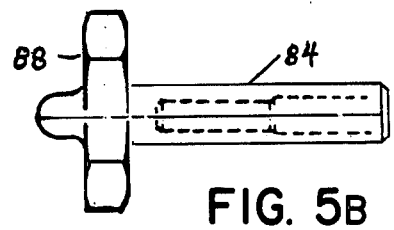
FIG. 5(b) is a side elevational view of the cam follower shown in FIG. 5(a) after a quarter rotation.

Referring now to the drawings, the disposable surgical cutting instrument 10 of the present invention has a drive housing 12 of generally cylindrical form designed to be easily held in the surgeons hand.

It should be noted at the outset that all parts of the invention which could possibly come in contact with the patient during an operation are sterilized and pyrogen free.

A protective latex sheath 14 is adapted to be placed over the drive housing 12 to protect the non sterile drive housing from contaminating when a surgical operation is performed. A disposable cutting head 16 is mounted on the drive housing 12 in engagement with the sheath 14. The disposable cutting head is driven by a drive shaft of a micro motor mounted in the drive housing so that only the cutting head 16 and sheath 14 comes into contact with blood, vitreous and other materials during an operation.

Figure 6:
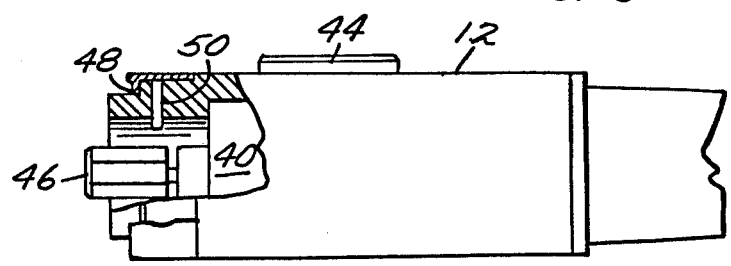
FIG. 6 is a side view of the motor end of the drive housing partially in section.
Figures 10, 11:
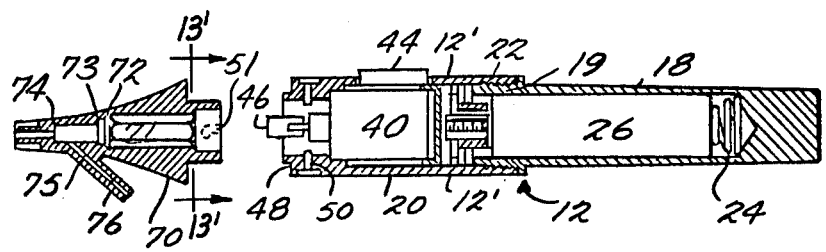
FIG. 10 discloses a cross sectional view of the cutter head housing.
FIG. 11 shows a cross sectional view of the drive housing.
Figure 12:
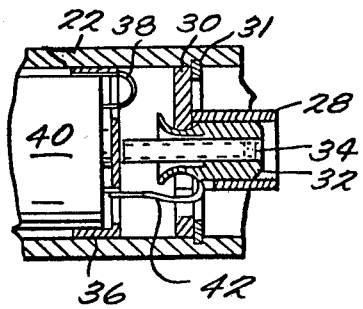
FIG. 12 discloses a partial enlarged cross sectional view of FIG. 11 taken along lines 12'—12'.
Figure 13:
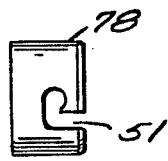
FIG. 13 discloses an enlarged side view of the end of the cutter head housing taken along lines 13'—13' of FIG. 10.

The drive housing 12 as shown in FIGS. 6–9, 11 and 12 is constructed of two components comprising a power source section 18 and a motor section 20. The power source section 18 has one end provided with an outer threaded surface 19 which is adapted to be screwed into a threaded inner surface 22 of the motor section to form the complete drive housing 12. A free seated coiled spring 24 is seated in one end of the power source section 18 and abuts against a battery 26 to urge the battery toward a standoff sleeve 28. The battery is slidably mounted in the housing for easy replacement and does not engage the standoff sleeve. The sleeve merely prevents electrical contact in case the battery is inadvertently installed backward. The standoff sleeve 28 is secured to a bulkhead 30 by adhesive means such as cement or press fit on the conductor. One end of the battery is engaged with a modified rivet contact 32 that is riveted in place. The bulkhead 30 is positioned within the motor housing section by a retaining ring 31 which is mounted in a channel cut in the housing. A set screw 34 contacts a motor support 36 mounted to the housing and holds the motor in place. A stripped wire 38 is bent and squeezed between the micromotor 40 and motor support 36 to form an electrical connection. The micromotor 40 is mounted in the motor housing and is electrically connected to the contact 32 by wire 42 so that when switch 44 is depressed an electrical contact is made between the battery and the micromotor, energizing the micromotor 40 to drive a hexagonal shaped drive shaft 46 of the micromotor. It should be noted that while the preferred embodiment discloses a hexagonal drive shaft 46, the drive shaft could be octagonal, square, flat or shaped in any other manner. The drive shaft end of the motor section forms a seat or channel 48 depending upon its construction and has two locking pins 50 protruding inwardly from the collar to fit bayonet slots 51 formed in the disposable cutting head 16. The drive housing is covered by using a sheath assembly 52 comprising a sleeve 54 having a tapered end 56 upon which the latex sheath 14 is stretched and mounted. The other end 58 of sleeve 54 is open and flanged outward so that the drive housing can be easily inserted into the mounted sheath.

The flexible latex sheath 14 has an open end 62 formed with a lip 64 which fits into the seat 48 defined in the motor section of the drive housing. The other end 66 of sheath 14 is closed. After the drive housing 12 has been deposited into the protective covering of the latex sheath the sleeve 54 is removed and lip 64 is inserted into the seat 48 formed in the end of the housing. The cutter head 16 is constructed with a body 70 having a varying diameter axial bore 71 cut therethrough. The bore 71 is cut in a series of steps so that the diameter narrows after each step. The steps form shoulders 69, 72, 73 and 74. Shoulder 73 is adapted to seat retainer ring 92, and seal 100.

The cutter head body 70 is provided with a second bore 75 and a tubular extension 76 axially aligned with the bore allowing a suction or irrigation device to communicate with bore 71. Thus a syringe 102 can be connected to the tubular extension 76 by a hose 104 to provide suction to a chamber portion 71(*a*) and the interior of tube 94 so that material severed by tube blade 95 travels through the tube into chamber portion 71(*a*), through bore 75 into a suitable disposal means such as the syringe 102. Alternatively, a saline solution or other suitable fluid can travel the same path through the cutter tube 94 to the eye.

The body 70 has a generally tapered exterior surface and is cut at one end in an annular manner to optionally receive a skirt 77 which is cemented to the annularly cut end of the body. The outer surface of the annularly cut end or tip 78 is provided with two bayonet slots 51. When the tip 78 is inserted into the motor section, the tip 78 fits around the hexagonal drive shaft 46 of the micromotor with the skirt 77 projecting over the outer surface of the motor section and the latex sheath 14.

A cam 80 also serving as a drive coupling member is positioned in the cutter body bore 71 and bears against retaining ring 93 which positions the cam in the cutter body bore 71. The cam 80 has an axial bore of hexagonal configuration at one end of its suitably shaped configuration to slidably receive and hold the drive shaft 46.

The cam 80 has a smooth inclined cam face 82 which contacts a cam follower assembly 84 held against the cam face by a coil spring 86. The cam follower assembly 84 comprises a face 88 which is hexagonal in shape slightly smaller than the hexagonal bore of the body which permits axial movement of the cam follower assembly but not rotation of the cam follower assembly. In this manner rotary movement of the cam is converted to reciprocating movement of the cam follower. Bearing against the reverse side of face 88 is a spring 86 which is seated against retaining ring 92 mounted in the bore of the body. The cutting tube blade 95 is mounted in the bore in the stem of the cam follower and reciprocates therewith. The tube blade 95 is positioned within the outer stationary tube 94 fixed to the end of the nose body in a cap member 97. The inner cutting tube blade 95 and the outer tube 94 may be of any configuration such as round, square, hexagonal, oval, octogonal, etc., so long as they are matched for a close telescoping fit in the area where cutting takes place. The outer tube 94 has an aperture 98 which may be of any preferred shape or size in the side wall near the end of the outer tube to permit entry of the vitreous material when suction is applied.

The relative length of the inner and the outer tube are such that the sharpened open end of the inner tube 94 passes across the aperture 98 with each down stroke of the cam. Each upstroke of the cam uncovers the aperture 98 to permit entry of the vitreous material. The upstroke is accomplished by the action of the coil spring 86 which is seated on retaining ring 92 pushing against the face of the cam follower and driving it towards the cam face. The down stroke action of the blade shears the vitreous material between the tube cutting end 99 of the inner blade 95 and the edge of the aperture. If desired the aperture 98 may be cut at an angle so as to provide the sharpest cutting surface possible. The cam follower assembly is mounted in the retainer ring which abuts a circular seal 100. The seal 100 prevents entry of foreign material from cavity 71(*a*) into the bore of the cutter head. The reciprocating cutter tube blade 95 is also provided with an aperture 101 which allows the sheared vitreous to be drawn upward through the inside diameter of the inner cutting tube and out through the opening 101 into the suction chamber 71(*a*) and then into the syringe 102.

The external fixed thin walled tube 94 projects from the end of the body 70 with the distal end 99 being formed into a smoothly blended closure. The other end 103 of the outer tube 94 is open. The open end is preferably press fitted into nose bushing 97, but it can be cemented if desired.

The clear plastic retainer ring 92 and seal 100 are mounted around the cam follower 84 to keep fluids from entering into the cavity housing the coupling means, thus preventing any leakage of vitreous material, fluid, blood or other materials past the shaft. The seal also prevents air from being drawn into the syringe via motor shaft leakage. The cam follower shaft 105 and ring 92 and seal 100 effectively seal off bore 71 to form the fluid receiving chamber 71(*a*).

A syringe 102 is connected to the tubular extension 76 by flexible tubing 104 which is inserted over the tubular extension 76 on one end and onto a female luer-lok of the syringe on the other end. Thus, suction or fluid can be transmitted to tube 95.

In the surgical operation and before the actual cutting of the vitreous is to take place, the surgeon takes the drive housing 12, drops it into the sleeve 54 made of a suitable material and into an associated sheath 14. The sleeve 54 is removed and sleeve lip 64 is inserted into the seat or channel 48 of the drive housing and the disposable plastic cutter head 16 is mounted on to the housing so that bayonet slots 51 cut into the cutter head are mounted over the pins 50 of the motor section with the cutter head then being depressed and turned so that it is locked into place on pins 50. Simultaneously, the outer skirt 77 extends down over the drive housing which is covered by flexible sheath 14. The lip 64 in combination with the drive housing and cutter head forms a fluid tight seal so that any fluid that might enter under skirt 77 is prevented from contacting the motor housing by sheath 14. The syringe 102 is then connected to the tubular extension 76 so that suction can be applied. When the opening is made in the anterior aqueous chamber the cutter tube blade 95 is inserted in the chamber. The surgeon depresses the switch 44 of the micro motor 40 through the protective sheath 14 thereby activating the motor and thereby rotating the cam 80 and reciprocating the cam follower 84 and associated tube blade. The tube blade 95 is constantly urged rearward through coil spring means 86 in the cutter head body. The spring means seats between the rear surface of the cam follower face and the cam follower retainer ring 92. As suction is applied to the instrument vitreous material is drawn into the aperture 98. The rapidly reciprocating spring loaded tube blade 95 fits flush against the aperture 98 and severs the vitreous. The suction carries the vitreous into the tube blade with the construction of the blade being such that the vitreous is passed through aperture 101 and is carried into chamber 71(a) of the cutter head and from there into a syringe or other suitable material disposal means.

The cutter of the present invention, although specifically designed for eye surgery could also be used to remove any other body tissue in the same manner. Because of the sealed nature of the internal structure of the cutter head, foreign materials cannot proceed past the seal 100 or chamber 71(a) so that no foreign materials contact the hexagonal drive shaft or interior of the drive housing. After the operation has been completed the surgeon rotates the cutter head thereby releasing it from its bayonet connection and removes the head from the drive housing. The head is then thrown away and the latex protective sheath 14 is removed from the drive housing so that the drive housing is ready for the next operation. When the next operation is ready to begin a new sterile disposable cutter head and a new sterile disposable sheath are placed on the instrument as previously indicated so that no problem of sterilizing the instrument is incurred with the external parts of the instrument being maintained in a sterile condition. This effectively eliminates patient-to-patient cross contamination.

In the foregoing description the invention has been described with reference to a particular preferred embodiment although it is to be understood that the specific details shown are merely illustrative and that the invention may be carried out in other ways without departing from the true spirit and scope of the following appended claims.

What is claimed is:

1. A surgical cutting device comprising a housing, motor means mounted inside said housing, means to energize said motor means, a shaft mounted to said motor means inside said housing, a cutter head removably secured to said housing, said cutter head comprising a body, an elongated tube secured to said cutter head body, a blade positioned in said tube and adapted to be reciprocated within said tube, said tube provided with an aperture therein to allow said blade to come in contact with tissue, drive transfer means mounted in said cutter head, said drive transfer means comprising a cam connected to said shaft, a cam follower assembly mounted in said cutter head engaging said cam, said blade means mounted to said cam follower thereby transmitting motion from said motor means to said blade means, said cutter head defining a passage-way communicating with said tube and adapted to supply a vacuum from an external source to said tube so that tissue sheared off by the reciprocation of said blade inside said tube will be carried off into said passageway.

2. A surgical instrument comprising a housing, motor means mounted in said housing and contained in said housing, said motor means being connected to a source of power, a removable sheath means mounted over said housing and surrounding said housing to protect said housing from external materials and contamination, and also to prevent cross contamination between successive operations, a cutter means removably mounted to said housing, said cutter means comprising a body, a tube projecting from said body, a blade means slidably mounted in said tube and mechanical drive transfer means mounted in said cutter means body, said mechanical drive transfer means connecting said blade means to said motor means for reciprocating movement of said blade means when said motor is activated, said tube defining an aperture in its side, said blade means in combination with the internal walls defining said tube aperture being adapted to shear tissue entering said hole, and a second passage means formed in said body and communicating with said tube to allow pressure differentials to be exerted to said tube.

3. A cutter means as claimed in claim 2 wherein said cutter means is disposable.

4. A surgical instrument as claimed in claim 2 wherein said source of power is battery means located within said housing.

5. A cutter means as claimed in claim 2 wherein said drive transfer means comprises a cam means removably connected to a drive shaft and adapted to be rotated by said drive shaft, a cam follower assembly mounted in said cutter means adapted to engage said cam and be reciprocated by said cam, spring means mounted around said cam follower assembly adapted to urge said blade means toward said drive housing.

6. The drive transfer means of claim 5 further comprising seal means surrounding said cam follower body adjacent a cam follower retaining ring which seal means serves to maintain a fluid tight seal between said cam follower and said blade.

7. The surgical instrument as claimed in claim 2 further including a source of vacuum connected to said body second passage means, said source of vacuum comprising a syringe connected to said second passage means by a hose means, said syringe being adapted to be activated by pulling the plunger out of the syringe to form a partial vacuum in the syringe and in the second passage means leading out to the aperture formed in said tube.

8. A surgical cutting apparatus comprising a drive housing, sheath means surrounding said drive housing and mounted to said drive housing, a removable cutting means mounted to said drive housing in engagement with said sheath means to form a fluid tight seal between said drive housing, sheath means and removable cutting means, motor means mounted in said drive housing, said motor means including a micromotor with a drive shaft, a source of power mounted in said drive housing, said motor means and source of power being enclosed in said drive housing, said removable cutting means comprising a cam means adapted to be connected to said motor shaft and blade means connected to a cam follower driven by said cam when said motor means is energized.

9. A surgical cutting apparatus as claimed in claim 8 wherein said cutting means comprises a body defining an axial bore, a cam follower assembly slidably mounted in said bore, said cam follower assembly comprising a coupling member, a tubular blade secured to one end of said coupling member, the other end of said coupling member being formed to engage a cam driven by said drive shaft, seal means surrounding said cam follower assembly dividing said axial bore into at least two separate compartments, said tubular blade defining an aperture therein.

10. A surgical cutting instrument as claimed in claim 8 wherein said sheath means comprises a flexible sack having a closed end and an open end with an annular lip.

11. A surgical cutting device for incising vitreous and other materials from the eye comprising an elongated tubular housing having an open end and a closed end, said tubular housing defining an opening in the side wall thereof adjacent the closed end, a tubular cutting member mounted coaxially within said tubular housing in sliding contact with the inner surface of said tubular housing, said tubular cutting member having a cutting edge facing said closed end of said tubular housing, mechanical actuation cam means for producing relative actual movement between said tubular housing and said tubular cutting member so that said tubular cutting member extends past said aperture of said tubular housing and incises substances drawn into said aperture in said tubular housing by acting in concert with the wall of said tubular housing defining said aperture, means coupling said tubular cutting member to a suction source to draw the incised substances from said housing up through said tubular cutting member and activation means to activate said mechanically actuated means said activation means being removably mounted to said elongated tubular housing.

12. A surgical cutting device for incising vitreous and other materials from the eye comprising an elongated tubular housing having an opened end and a closed end, said tubular housing defining an opening in the side wall thereof adjacent the closed end, a tubular cutting member mounted coaxially within said tubular housing in sliding contact with the inner surface of said tubular housing, said tubular member having an opening in the side wall, providing a passage for vitreous material and the like into the tubular housing allowing removal of materials from the interior of said housing, said tubular member having a cutting edge facing said closed end of said tubular housing, mechanically actuated cam means for producing relative actual movement between said tubular housing and said tubular member so that said tubular member incises material drawn into said aperture in said tubular housing by acting in concert with the wall of said tubular housing, said opening providing communication of said tubular member to a suction pressure source to draw the incised material up through said tubular member and from said housing and means to activate said mechanically actuated cam means removably mounted to said elongated tubular housing, said activation means comprising an enclosed power source and motor mounted in said tubular housing, said cam means comprising a cam connected to said motor and a cam follower means engaging said cam, said cam follower means comprising a body with said tubular members being mounted to said body.

* * * * *